United States Patent
Abe et al.

(10) Patent No.: US 9,303,247 B2
(45) Date of Patent: Apr. 5, 2016

(54) PROLIFERATING AGENT FOR MONOCYTE, CULTURE MEDIUM FOR PROLIFERATING MONOCYTE, METHOD FOR PRODUCING MONOCYTE, METHOD FOR PRODUCING DENDRITIC CELL, AND METHOD FOR PRODUCING DENDRITIC CELL VACCINE

(71) Applicants: Hakushinkouseikai Foundation, Tokyo (JP); Life Science Research Institute Ltd., Tokyo (JP)

(72) Inventors: Hiroyuki Abe, Tokyo (JP); Hiroaki Kawasaki, Tokyo (JP)

(73) Assignees: HAKUSHINKOUSEIKAI FOUNDATION (JP); LIFE SCIENCE RESEARCH INSTITUTE LTD. (JP)

( * ) Notice: Subject to any disclaimer, the term of this patent is extended or adjusted under 35 U.S.C. 154(b) by 0 days.

(21) Appl. No.: 14/343,240

(22) PCT Filed: Feb. 8, 2013

(86) PCT No.: PCT/JP2013/053154
§ 371 (c)(1),
(2) Date: Mar. 6, 2014

(87) PCT Pub. No.: WO2013/118899
PCT Pub. Date: Aug. 15, 2013

(65) Prior Publication Data
US 2015/0030634 A1  Jan. 29, 2015

(30) Foreign Application Priority Data

Feb. 10, 2012 (JP) ................................ 2012-027332

(51) Int. Cl.
*C12N 5/0786* (2010.01)
*C12N 5/0784* (2010.01)
*A61K 39/00* (2006.01)

(52) U.S. Cl.
CPC .......... *C12N 5/0639* (2013.01); *A61K 39/0011* (2013.01); *C12N 5/0645* (2013.01); *A61K 2039/5154* (2013.01); *C12N 2501/22* (2013.01); *C12N 2501/2303* (2013.01); *C12N 2501/24* (2013.01); *C12N 2501/26* (2013.01); *C12N 2506/115* (2013.01)

(58) Field of Classification Search
CPC ............. C12N 2501/23; C12N 5/0639; C12N 2501/22; C12N 2501/26; C12N 2506/115; A61K 2039/5154
See application file for complete search history.

(56) References Cited

U.S. PATENT DOCUMENTS 5,851,756 A * 12/1998 Steinman et al. .................. 435/2
6,017,527 A * 1/2000 Maraskovsky et al. ..... 424/93.71
6,479,286 B1 * 11/2002 Nelson et al. ................. 435/377
2004/0203143 A1 10/2004 Tjoa et al.
2006/0002899 A1 1/2006 Rice et al.
2006/0269526 A1 11/2006 Galipeau et al.

FOREIGN PATENT DOCUMENTS

| EP | 1604016 B1 | 1/2009 |
|---|---|---|
| JP | 2006-519021 A | 8/2006 |
| JP | 2010-515442 A | 5/2010 |
| WO | 9853048 A1 | 11/1998 |
| WO | 02067760 A2 | 9/2002 |
| WO | 2004020613 A1 | 3/2004 |
| WO | 2004/076651 A2 | 9/2004 |

OTHER PUBLICATIONS

Suzuki et al. Am J Hematol. Apr. 2004;75(4):179-189.*
IPER for PCT/JP2013/053154 (Aug. 12, 2014).*
Sekar et al., Journal of Leukocyte Biology vol. 88 No. 2 413-424 (2010).*
Daro et al., Cytokine, 17(3):119-130 (2002).*
Chen, Ben D-M., et al., "Interleukin 3 (IL 3) regulates the in vitro proliferation of both blood monocytes and peritoneal exudate macrophages: synergism between a macrophage lineage-specific colony-stimulating factor (CSF-1) and IL 3", Journal of Immounology, 1986, vol. 137, No. 2, pp. 563-570.
Ju, Songwen, et al., "A novel approach to induce human DCs from monocytes by triggering 4-1BBL reverse signaling", International Immounology, 2009, vol. 21, No. 10, pp. 1135-1144.
Rojas, Darling, et al., "IFN-? generates maturation-arrested dendritic cells that induce T cell hyporesponsiveness independent of Foxp3+ T-regulatory cell generation", Immounology Letters, 2010, vol. 132, No. 1-2, pp. 31-37.
Shurin, Michael R. et al., "FLT3 Ligand Induces the Generation of Functionally Active Dendritic Cells in Mice", Cellular Immunology, 1997, vol. 179, pp. 174-184.
Xu, Hui, et al., "Dendritic cells differentiated from human monocytes through a combination of IL-4, GM-CSF and IFN-gamma exhibit phenotype and function of blood dendritic cells", Advances in experimental medicine and biology, 1995, vol. 378, No. 2, pp. 75-78.
Zou, G. M., et al., "Cytokines in the generation and maturation of dendritic cells: recent advance", European Cytokine Network, 2002, vol. 13, No. 2, pp. 186-199.
International Search Report for International Application No. PCT/JP2013/053154, dated Mar. 19, 2013, with English translation.
(Continued)

*Primary Examiner* — Daniel C Gamett
(74) *Attorney, Agent, or Firm* — Cantor Colburn LLP

(57) ABSTRACT

The purpose of the present invention is to provide a means for proliferating a monocyte with high efficiency and in a simple manner. The present invention provides a proliferating agent for a monocyte, which consists of at least one component selected from Flt-3L, IL-3 and IFN-γ and can be used before a treatment for differentiation of a monocyte into a dendritic cell. The present invention also provides a culture medium for use in the proliferation of a monocyte, which contains at least one component selected from Flt-3L, IL-3 and IFN-γ and can be used before a treatment for differentiation of a monocyte into a dendritic cell. The culture medium for use in the proliferation of a monocyte according to the present invention may contain GM-CSF.

13 Claims, 3 Drawing Sheets

(56) References Cited

OTHER PUBLICATIONS

Notice of Reasons for rejection issued to JP Application No. 2013-541894, mailed Jan. 7, 2014. No English translation available.

Xu et al., "Dendritic Cells Differentiated from Human Monocytes through a combination of IL-4, GM-CSF and IFN-γ Exhibit Phenotype and Function of Blood Dendritic Cells", Advances in Experimental Medicine and Biology: vol. 378, Dendritic Cells in Fundamental and Clinical Immunology: vol. 2, 1995, pp. 75-78.

Ju, Songwen et al, "A Novel Approach to Induce Human DCs from Monocytes by Triggering 4-1BBL Reverse Signaling", International Immunology, 2009, vol. 21, No. 10, pp. 1135-1144.

Chen, Ben D-M et al, "Interleukin 3 (IL 3) Regulates the In Vitro Proliferation of Blood Monocytes and Peritoneal Exudate Macrophages: Synergism between a Macrophage Lineage-Specific Colony-Stimulating Factor (CSF-1) and IL 3", The Journal Immunology, 1986, vol. 137, No. 2, pp. 563-570.

Chinese Office Action regarding Patent Application No. 201380001273.1; Date of Mailing: Aug. 18, 2014, English Translation Not Available.

Yao Qin, "Clinical and Experimental Study on Peripheral Blood Dendritic Cell (DCs) Vaccines in the Treatment of Gynecological Malignancies," Asia-Pacific Traditional Medicine; Sep. 2011, pp. 79-80, vol. 7, No. 9, with English abstract.

Extended European search report issued to EP Application No. 13746292.5, mailed Dec. 18, 2014.

Julie Patenaude et al: "LPS response and endotoxin tolerance in Flt-3L-induced bone marrow-derived dendritic cells", Cellular Immunology, Academic Press, San Diego, CA, US, vol. 271, No. 1, Jun. 20, 2011, pp. 184-191, XP028284105.

K. A. Ward et al: "CD34+-derived CD11c+++ BDCA-1++ CD123++ DC: expansion of a phenotypically undescribed myeloid DC1 population for use in adoptive immunotherapy", Cytotherapy, vol. 8, No. 2, Jan. 1, 2006, pp. 130-140, XP055156162.

Shalin H Naik et al: "Development of plasmacytoid and conventional dendritic cell subtypes from single precursor cells derived in vitro and in vivo", Nature Immunology, vol. 8, No. 11, Oct. 7, 2007, pp. 1217-1226, XP055154963.

Tae Hee Han et al: "Evaluation of 3 Clinical Dendritic Cell Maturation Protocols Containing Lipopolysaccharide and Interferon-[gamma]", Journal of Immunotherapy, vol. 32, No. 4, May 1, 2009, pp. 399-407, XP055156169.

Written Opinion corresponding to Singapore Application No. 11201404570W; Date of Written Opinion: Apr. 29, 2015.

Chinese Office Action corresponding to Application No. 201380001273.1; Date of Mailing: Aug. 19, 2015.

Development and homeostasis of dendritic cells, Kang Liu, et al., Eur. J. Immunol. 2010. 40: 2085-2130.

Cheung D.L. And Hamilton J.A., Regulation of human moncyte DNA synthesis by colony-stimulating factors, cytokines, and cyclic adenosine monophosphate. Blood, Apr. 15, 1992, vol. 79, No. 8, pp. 1972-1981.

Written Opinion corresponding to Singapore Application No. 11201404570W; Date of Mailing: Oct. 23, 2015.

* cited by examiner

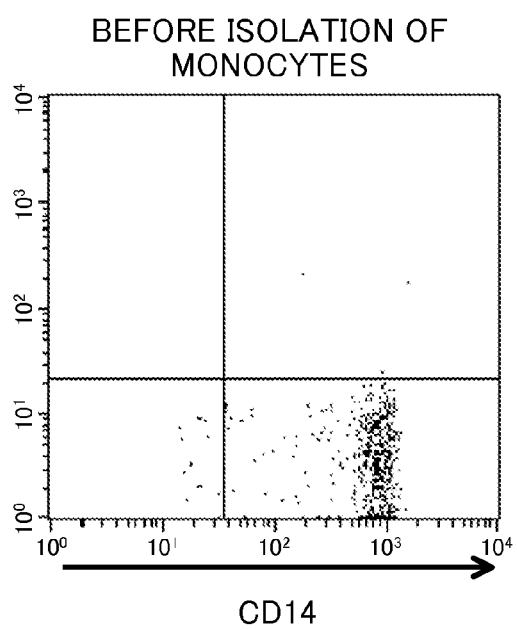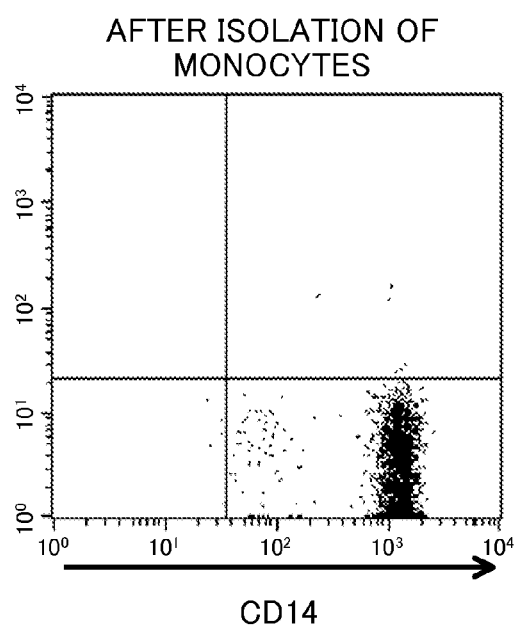

PROLIFERATING AGENT FOR MONOCYTE, CULTURE MEDIUM FOR PROLIFERATING MONOCYTE, METHOD FOR PRODUCING MONOCYTE, METHOD FOR PRODUCING DENDRITIC CELL, AND METHOD FOR PRODUCING DENDRITIC CELL VACCINE

This is the U.S. national stage of application No. PCT/JP2013/053154, filed on 8 Feb. 2013. Priority under 35 U.S.C. §119(a) and 35 U.S.C. §365(b) is claimed from Japanese Application No. 2012-027332, filed 10 Feb. 2012, the disclosure of which is also incorporated herein by reference.

TECHNICAL FIELD

The present invention relates to a monocyte proliferating agent, a monocyte proliferating culture medium, a method of producing monocytes, a method of producing dendritic cells, and a method of producing a dendritic cell vaccine.

BACKGROUND ART

Recently, use of dendritic cell vaccines in cancer treatment is gathering attention. The dendritic cell vaccine is prepared from dendritic cells derived from a subject (e.g., a cancer patient) to which the vaccine is administered, wherein a cancer antigen is incorporated into the dendritic cells (pulsed with a cancer antigen), and the vaccine is administered to the subject in vivo. The administered dendritic cells present the cancer antigen to T-cells, and the T-cells (CTL) presented with the antigen specifically attack cancer cells. It is therefore possible to treat cancer without damaging in vivo normal cells.

Incidentally, the dendritic cells necessary for producing a dendritic cell vaccine cannot be directly isolated from the body. Accordingly, dendritic cells are prepared by isolating monocytes from blood sampled from a subject to which the vaccine is administered and differentiating the monocytes into dendritic cells.

As a conventionally known method of sampling monocytes for producing a dendritic cell vaccine, a method of isolating leukocytes in blood with a blood component collecting apparatus (hereinafter, this method is referred to as "apheresis") is known. In the apheresis, however, the practical use of the apparatus is expensive and the operation of the apparatus requires advanced skills. In addition, the apheresis collects a mixture containing not only monocytes but also components other than monocytes (e.g., leukocytes, erythrocytes, and platelets). Accordingly, a step of isolating mononuclear cells for removing components other than monocytes, such as erythrocytes and platelets, is usually performed after the apheresis.

In clinical application of a dendritic cell vaccine, approximate $1 \times 10^7$ cells are desirably used for one administration. In order to prepare such a number of cells, apheresis is usually carried out about eight times using one subject at intervals. Furthermore, since the ratio of monocytes contained in blood is small, if apheresis is employed for obtaining a sufficient amount of monocytes for producing a dendritic cell vaccine, it is necessary to sufficiently collect the leukocyte components by circulating the blood in an apheresis apparatus. This puts a very large burden on a patient physically and temporally. Accordingly, if the condition of the patient suddenly worsens during apheresis, the apheresis is discontinued, and the dendritic cell vaccine therapy itself must be abandoned in some cases. It is alleged that the amount of monocyte components collected by apheresis usually allows production of a dendritic cell vaccine that can be administered for about five to eight times, but the actual amount of the resultant dendritic cell vaccine varies depending on the blood conditions and other factors of a patient.

In a conventional method of collecting peripheral blood from, for example, an arm, the burden on a patient is light, but the method has a disadvantage that when the collected monocytes are directly differentiated into dendritic cells by a conventional method, a sufficient number of cells cannot be obtained. Accordingly, in order to produce a dendritic cell vaccine composed of a sufficient number of cells from monocytes prepared from collected peripheral blood, proliferation of the monocytes in the process of producing the vaccine is a problem to be solved, and a technology for overcoming it has been demanded. In such a technology, the period of time for producing a dendritic cell vaccine is desirably about two weeks in view of the dosing interval of the dendritic cell vaccine.

Accordingly, in order to solve the problem, in vitro proliferation of monocytes isolated from blood is proposed. As such a method, Patent Literature 1 discloses the culture of monocytes while preventing a specific material in the monocyte from being expressed. This method, however, needs a step of producing a recombinant and takes a long time for the culture. [Patent Document 1] Japanese Unexamined Patent Application (Translation of PCT Application), Publication No. 2010-515442

DISCLOSURE OF THE INVENTION

Problems to be Solved by the Invention

It is an object of the present invention to provide a method allowing highly efficient and simple proliferation of monocytes.

Means for Solving the Problems

The present inventors have found that a specific cytokine involved in, for example, proliferation of hematopoietic stem cells can allow monocytes to highly efficiently proliferate and, as a result, have completed the present invention. The present invention specifically provides the followings:

(1) A monocyte proliferating agent consisting of at least one of Flt-3L, IL-3, and IFN-γ and being used before treatment for differentiating monocytes into dendritic cells;

(2) A monocyte proliferating culture medium containing at least one of Flt-3L, IL-3, and IFN-γ and being used before treatment for differentiating monocytes into dendritic cells;

(3) The monocyte proliferating culture medium according to aspect (2), further comprising GM-CSF;

(4) A method of producing monocytes, the method comprising a proliferation step of culturing a monocyte material in the monocyte proliferating culture medium according to aspect (2) or (3) for allowing monocytes to proliferate;

(5) The method of producing monocytes according to aspect (4), wherein the monocyte material is a mixture containing monocytes and a leukocyte component other than monocytes;

(6) The method of producing monocytes according to aspect (4) or (5), the method further comprising a reduction step of reducing the content of a component other than monocytes in body fluid to obtain the monocyte material, before the proliferation step;

(7) The method of producing monocytes according to aspect (6), wherein the reduction is performed using a magnetic bead having a higher affinity to at least one of monocytes, leukocyte components other than monocytes, plasma, and erythrocytes in the monocyte material than the others;

(8) The method of producing monocytes according to aspect (6) or (7), wherein the monocyte material is prepared from 100 mL or less of peripheral blood;

(9) The method of producing monocytes according to any one of aspects (6) to (8), the method not comprising a cryopreservation step of cryopreserving the monocytes;

(10) A method of producing dendritic cells, the method comprising:

a monocyte production step of producing monocytes by the method of producing monocytes according to any one of aspects (4) to (9); and a differentiation step of differentiating the monocytes prepared in the monocyte production step into dendritic cells;

(11) The method of producing dendritic cells according to aspect (10), wherein in the differentiation step, the monocytes are cultured in a culture medium containing at least one of Flt-3L, IL-3, and IFN-γ;

(12) The method of producing dendritic cells according to aspect (10) or (11), the method further comprising a pulse step of pulsing the dendritic cells;

(13) A method of producing a dendritic cell vaccine, the method comprising:

a dendritic cell-producing step of producing dendritic cells by the method of producing dendritic cells according to any one of aspects (10) to (12); and a preparation step of preparing a dendritic cell vaccine from the dendritic cells produced in the dendritic cell-producing step;

(14) The method of producing a dendritic cell vaccine according to aspect (13), the method not comprising a cryopreservation step of cryopreserving at least one of the monocytes and the dendritic cells; and

(15) The method of producing a dendritic cell vaccine according to aspect (13) or (14), wherein the monocyte material is prepared from body fluid collected from a subject to which the dendritic cell vaccine is administered.

Effects of the Invention

Accordingly, the present invention provides a method allowing highly efficient and simple proliferation of monocytes.

BRIEF DESCRIPTION OF THE DRAWINGS

FIG. 1 includes graphs showing the number of monocytes contained in each cell sample ($3 \times 10^5$ cells) before isolation (A) and after isolation (B) of monocytes from peripheral blood.

PREFERRED MODE FOR CARRYING OUT THE INVENTION

Figure 2:
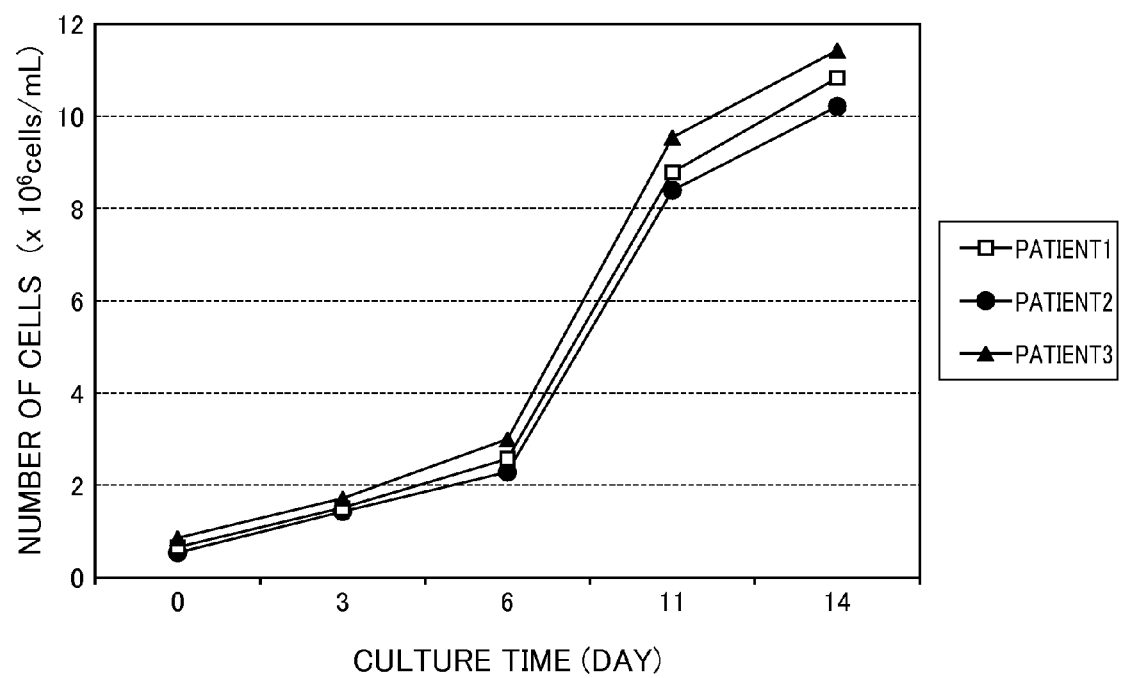
FIG. 2 is a graph showing changes in the number of cells with time when monocytes were cultured in the presence of the monocyte proliferating agent according to an embodiment of the present invention for 3 days and were then differentiated into dendritic cells by culture for 11 days.

Embodiments of the present invention will now be described, but these embodiments are not intended to limit the present invention.

Monocyte Proliferating Agent

The monocyte proliferating agent of the present invention is composed of at least one of Flt-3L, IL-3, and IFN-γ and is used before treatment for differentiating monocytes into dendritic cells. The monocyte proliferating agent of the present invention may be used in any state without particular limitation. In general, the agent is added to a culture medium capable of culturing monocytes or is premixed with a culture medium as a component.

The phrase "treatment for differentiating monocytes into dendritic cells" refers to culture of monocytes under conditions suitable for differentiating monocytes into dendritic cells, i.e., in the presence of a predetermined amount of a specific cytokine (e.g., GM-CSF, IL-4, or IL-6). It is known that the number of monocytes also increases to some extent during the process of differentiation treatment. The monocyte proliferating agent of the present invention is, however, not used in this differentiation treatment, but is used in a stage prior to the treatment.

The amount of each cytokine for allowing monocytes to differentiate into dendritic cells refers to an amount of a cytokine allowing the number of dendritic cells to become 20% or more relative to the total number of cells when the monocytes are cultured under conditions of 37° C. and 5% $CO_2$ for 6 days in a culture medium containing the cytokine at such an amount. The specific amount varies depending on the components of a culture medium and the conditions of culture.

The monocyte proliferating agent of the present invention can allow monocytes to proliferate to a sufficient number (e.g., $10^6$ to $10^7$ cells/mL or more) for producing a dendritic cell vaccine before subjecting the monocytes to the differentiation treatment. Consequently, a dendritic cell vaccine can be produced without repeating the step of culturing monocytes several times and can therefore be simply produced.

Flt-3L (Flt3-Ligand), IL-3 (interleukin-3), and IFN-γ (interferon-γ) are known as cytokines involved in, for example, proliferation of hematopoietic stem cells. The present inventors have investigated them and, as a result, have found surprisingly that these cytokines effectively allow the proliferation of monocytes.

Flt-3L

The amount of Flt-3L suitable for proliferation of monocytes is not particularly limited and may be 100 to 10000 IU/mL, preferably 1000 to 5000 IU/mL, and most preferably 1000 to 3000 IU/mL in a culture medium capable of culturing monocytes.

IL-3

The amount of IL-3 suitable for proliferation of monocytes is not particularly limited and may be 100 to 10000 IU/mL, preferably 100 to 5000 IU/mL, and most preferably 500 to 3000 IU/mL in a culture medium capable of culturing monocytes.

IFN-γ

The amount of IFN-γ suitable for proliferation of monocytes is not particularly limited and may be 1 to 1000 ng/mL, preferably 1 to 500 ng/mL, and most preferably 1 to 50 ng/mL in a culture medium capable of culturing monocytes.

The monocyte proliferating agent of the present invention may comprise any one of Flt-3L, IL-3, and IFN-γ alone or may comprise a combination of two or more thereof. As described above, since Flt-3L, IL-3, and IFN-γ have similar functions, it is believed that use in a combination thereof will not cause inhibition of functions among each other. In a combination of two or more of these cytokines, the amount of each cytokine may be within the range mentioned above or may be less than the range.

Whether the cells proliferated with the monocyte proliferating agent of the present invention are monocytes or not is confirmed by analysis of a cell surface marker of the obtained cells by flow cytometry. The cell surface marker of the monocyte is, for example, CD14. A cell having such a marker is recognized to be a monocyte.

Monocyte Proliferating Culture Medium

The monocyte proliferating culture medium of the present invention contains at least one of Flt-3L, IL-3, and IFN-γ and is used before treatment for differentiating monocytes into dendritic cells. Specifically, the monocyte proliferating culture medium can further contain a nutritional component, a pH adjuster, and other components for enabling culture of monocytes. The culture medium containing such components is not particularly limited, and examples thereof include serum-free synthetic culture media for lymphocytes, AIM-V, and RPMI-1640. The term "culture medium" throughout the specification encompasses media in liquefied prepared forms and also component mixtures (usually powder) before preparation.

The monocyte proliferating culture medium of the present invention may further contain a cytokine (granulocyte macrophage colony-stimulating factor (GM-CSF)) involved in differentiation of monocytes.

A monocyte tends to differentiate into a macrophage in the presence of GM-CSF and tends to differentiate into a dendritic cell in the presence of GM-CSF and IL-4. The investigation by the present inventors, however, revealed a fact that the monocyte proliferating culture medium of the present invention containing GM-CSF can considerably accelerate proliferation of monocytes. It has been conventionally known that GM-CSF itself also has an effect of allowing proliferation of monocytes, however, the monocyte proliferating culture medium of the present invention containing GM-CSF can considerably accelerate proliferation of monocytes without differentiating the monocytes. In addition, the monocyte proliferating culture medium of the present invention may further contain IL-4 in an amount less than the amount allowing differentiation of monocytes into dendritic cells (e.g., 500 to 2000 IU/mL), in addition to GM-CSF. The amount of GM-CSF contained in the monocyte proliferating culture medium of the present invention is, for example, within a range of 500 to 2000 IU/mL.

The monocyte proliferating culture medium of the present invention may contain a reagent that is usually used in cell culture. Examples of the reagent include antibiotics (e.g., gentamycin and kanamycin), albumin, and serum (e.g., fetal bovine serum). The monocyte proliferating culture medium of the present invention may contain autologous plasma (i.e., the monocytes to be proliferated and the autologous plasma are collected from the same body) derived from a living body (mammals such as human, porcine, bovine, horse, goat, sheep, rabbit, kangaroo, or monkey). Furthermore, the monocyte proliferating culture medium of the present invention may contain a material for accelerating differentiation induction to dendritic cells, such as picibanil chloride or prostaglandin E2 (PGE2).

Method of Producing Monocytes

The method of producing monocytes of the present invention includes a proliferation step of culturing a monocyte material in the monocyte proliferating culture medium of the present invention to allow the monocytes to proliferate.

Proliferation Step

The proliferation step according to the present invention may be performed under any condition without particular limitation, and from the viewpoint of allowing monocytes to proliferate before the start of differentiation of a lot of monocytes, the culture is preferably performed under conditions of 30° C. to 40° C. and 2% to 8% $CO_2$. The period of culture time can be appropriately controlled depending on the necessary amount of monocytes and may be 3 to 20 days, 3 to 18 days, 3 to 14 days, or 3 to 10 days. During the culture, replacement of the culture medium may be appropriately carried out by a known method.

According to the method of producing monocytes of the present invention, the monocytes in a monocyte material can proliferate to an amount allowing clinical use (e.g., $10^6$ to $10^7$ cells/mL or more) within a short culture time such as 14 days. The amount allowing clinical use refers to an amount of monocytes proliferated such that a dendritic cell vaccine prepared from dendritic cells differentiated from the proliferated monocytes can be directly used as a vaccine without being subjected to freezing treatment.

In the method of producing monocytes of the present invention, monocytes are cultured in the monocyte proliferating culture medium of the present invention, that is, monocytes are proliferated under conditions giving a less burden on the monocytes. Consequently, the method of producing monocytes of the present invention can be expected to provide monocytes with a high vital cell ratio (e.g., higher than 90%).

Monocyte Material

The monocyte material in the present invention is a specimen containing monocytes. The monocyte material may be composed of monocytes only. Alternatively, since the method of producing monocytes of the present invention can allow selective and efficient proliferation of monocytes, the monocyte material may be a mixture containing monocytes and a leukocyte component (e.g., lymphocytes, NK cells, or NKT cells) other than monocytes. This mixture may further contain plasma and erythrocytes. The mixture may be a mononuclear cell fraction mainly containing monocytes and lymphocytes prepared from a body fluid sample such as blood by, for example, density gradient centrifugation.

Reduction Step

It is preferred to perform the reduction step for preparing the monocyte material by reducing the content of components other than monocytes in the body fluid, before the proliferation step. The reduction can be performed by, for example, a method using a magnetic bead, density gradient centrifugation, a method of isolating monocytes in components of body fluid by means of adhesion of only the monocytes to a petri dish, or a combination thereof.

The magnetic bead can collect monocytes simply and with a high yield and causes less damages to the monocytes. Its use is therefore preferred. The magnetic bead has a higher affinity to monocytes or at least one (preferably all) of leukocyte components other than monocytes, plasma, erythrocytes in the monocyte material than the others. Such a magnetic bead may have a structure in which, for example, an antibody to the material to be isolated is bound to a magnetic carrier. If a mononuclear cell fraction prepared by density gradient centrifugation of body fluid is treated with a magnetic bead, the yield of monocytes is advantageously further increased.

Use of a magnetic bead having a relatively high affinity to monocytes can mainly isolate monocytes from body fluid (this is referred to as monocyte positive selection). A monocyte material is obtained by removing the magnetic bead from the isolated monocytes by a known method. This embodiment is advantageous in the point that the number of types of necessary magnetic beads is small, but it needs a step of removing the magnetic beads from monocytes, and damage to the monocytes is slightly worried.

Use of a magnetic bead having a relatively high affinity to at least one of leukocyte components other than monocytes, plasma, and erythrocyte can remove components other than monocytes from body fluid (this is referred to as monocyte negative selection). As a result, a monocyte material mainly containing monocytes is prepared. This embodiment is disadvantageous in the point that the number of types of necessary magnetic beads is large, but it does not need a step of removing the magnetic beads from monocytes and can certainly provide good quality monocytes and is therefore preferred. The sample to be subjected to the monocyte negative selection may be a mononuclear cell fraction prepared by density gradient centrifugation of body fluid. In this case, a magnetic bead having a relatively high affinity to lymphocytes is used.

In a case of using a magnetic bead, a magnetic cell separator can be used. The magnetic cell separator isolates monocytes from body fluid based on a predetermined program by setting reagents such as a magnetic bead, together with a body fluid sample such as blood, in the separator. The use of such an apparatus can isolate monocytes from body fluid rapidly and with a high yield and is therefore preferred. Isolation of monocytes with a high yield can significantly increase the proliferation efficiency of monocytes with the monocyte proliferating agent of the present invention.

A preferable example of the magnetic cell separator in the present invention is "RoboSep (trademark)" (VERITAS Corporation).

Body Fluid

Examples of samples to prepare the monocyte material include body fluid such as blood and bone marrow fluid. The blood is collected from a living body (e.g., a human cancer patient), and examples thereof include peripheral blood and cord blood. In particular, peripheral blood is preferred from the viewpoint of reducing the burden on the subject. The body fluid may be collected by any method without particular limitation and may be collected from a region such as an arm, wrist, or foot using, for example, a syringe or winged needle. Since the method of producing monocytes of the present invention can be performed with a small amount of body liquid, the burden (e.g., cost and time) on the living body from which the body fluid is collected is significantly low, compared to conventional methods such as apheresis.

Conventionally, in order to produce a dendritic cell vaccine, a large amount, such as 300 to 400 mL, of blood has been collected from a living body. In the method of producing monocytes of the present invention, however, the amount of body fluid used may be small, such as 100 mL or less, 90 mL or less, 80 mL or less, 70 mL or less, 60 mL or less, 50 mL or less, 40 mL or less, 35 mL or less, 30 mL or less, 25 mL or less, 20 mL or less, 15 mL or less, 10 mL or less, 5 mL or less, 1 mL or less, or 0.5 mL or less. The lower limit of the amount of body fluid is not particularly determined and may be 0.1 mL or more for example.

The monocytes prepared by the method of producing monocytes of the present invention may be directly differentiated into dendritic cells through a differentiation step or may be cryopreserved by a conventionally known method. The cryopreserved monocytes can be subjected to the differentiation step of monocytes after thawing. However, from the viewpoint of avoiding a loss of monocytes that can be differentiated, the monocytes preferably are not cryopreserved. In the present invention, since monocytes for being subjected to the differentiation step can be obtained without performing repetition of culture of monocytes several times, the monocytes can be supplied to the differentiation step of the monocytes without undergoing cryopreservation.

Method of Producing Dendritic Cells

The method of producing dendritic cells of the present invention includes a monocyte production step of producing monocytes by the method of producing monocytes of the present invention and a differentiation step of differentiating the monocytes prepared in the monocyte production step into dendritic cells.

Differentiation Step

The method of differentiating monocytes into dendritic cells is a conventionally known step. That is, monocytes are differentiated into immature dendritic cells by culture in a culture medium for differentiation containing, for example, IL-4. The resultant immature dendritic cells are differentiated into mature dendritic cells by culture in a culture medium containing, for example, TNF-α. The term "dendritic cell" in the present invention encompasses both an immature dendritic cell and a mature dendritic cell.

Also in the differentiation step of the present invention, a culture medium containing at least one of Flt-3L, IL-3, and IFN-γ is preferably used. Such a culture medium allows differentiation of monocytes into dendritic cells while allowing proliferation of monocytes, resulting in production of a larger number of dendritic cells. However, when a sufficient number of monocytes can be prepared in the proliferation step or when the necessary number of dendritic cells is not large, the culture medium may not contain the above-mentioned components.

Pulse Step

Dendritic cells capable of presenting a desired antigen can be prepared by incorporating, for example, a material (e.g., peptide) extracted from cancer cells, a cancer-specific antigen, or an artificial antigen into the resulting immature dendritic cells or mature dendritic cells (pulsing with such a material). The pulse step may be performed during the process of producing dendritic cells or may be performed during the process of preparing a vaccine after the production of dendritic cells as described below.

The method of pulsing is not particularly limited as long as a desired antigen is incorporated into dendritic cells and is performed by, for example, culturing dendritic cells in the presence of a desired antigen. In general, an antigen is incorporated into immature dendritic cells easier than into mature dendritic cells. The pulsing is therefore preferably performed using immature dendritic cells.

Whether the resulting cells are dendritic cells or not is confirmed by analysis of a cell surface marker of dendritic cells by flow cytometry. The cell surface marker of the dendritic cell is, for example, CD83. A cell having such a marker is recognized to be a dendritic cell.

Whether the dendritic cells prepared by the method of producing dendritic cells of the present invention have antigen-presenting ability or not is confirmed by analysis of a cell surface marker of dendritic cells by flow cytometry. Examples of the cell surface marker of the dendritic cell having antigen-presenting ability include MHC class I molecules (HLA-A, B, and C) and MHC class II molecules (HLA-DR). A dendritic cell having such a marker is recognized to have antigen-presenting ability.

Method of Producing a Dendritic Cell Vaccine

The method of producing a dendritic cell vaccine of the present invention includes a dendritic cell-producing step of producing dendritic cells by the method of producing dendritic cells of the present invention and a preparation step of preparing a dendritic cell vaccine from the dendritic cells produced in the dendritic cell-producing step.

Preparation Step

The dendritic cell vaccine may be prepared from dendritic cells by any method without particular limitation. For example, the dendritic cells are mixed with an agent (such as physiological saline or a Ringer solution) that is commonly formulated in a vaccine preparation. When dendritic cells not yet subjected to the pulse step are used, the dendritic cells are subjected to the pulse step.

The method of producing a dendritic cell vaccine of the present invention may not include a cryopreservation step of cryopreserving at least one of the monocytes and the dendritic cells. In the method of producing a dendritic cell vaccine of the present invention, a sufficient amount of monocytes or dendritic cells for producing a dendritic cell vaccine can be prepared in a short period of time, and a dendritic cell vaccine can be timely prepared without requiring a store of monocytes or dendritic cells. Therefore, monocytes or dendritic cells optionally produced can be used without subjecting to cryopreservation for producing a dendritic cell vaccine. Consequently, damage of cells and a reduction in antigen-presenting ability of the dendritic cells by freezing can be avoided.

The resulting dendritic cell vaccine can be administered in vivo by a conventionally known method such as intradermal injection.

The monocyte material is preferably prepared from body fluid collected from a subject to which the dendritic cell vaccine is administered. The dendritic cell vaccine reduced in harmful side effects can be prepared by using a monocyte material derived from a subject to which the dendritic cell vaccine is administered. However, as long as the immune reaction occurring by administration of the dendritic cell vaccine is acceptable, body fluid collected from a subject other than the subject to which the vaccine is administered may be used.

EXAMPLES

The present invention will now be described based on examples of the present invention, but the present invention is not limited to the following examples.

Example 1

Isolation of Monocytes

Peripheral blood (25 mL) was collected from the arm of each of three cancer patients. Cells of a mononuclear cell fraction were obtained by subjecting each peripheral blood to density gradient centrifugation using a Ficoll solution (GE Healthcare Japan Corporation). The resulting cells of the mononuclear cell fraction were set to a magnetic cell separator (trade name: RoboSep, VERITAS Corporation), and $CD14^+$ monocytes and $CD16^+$ monocytes were isolated according to the program set for monocyte isolation.

The numbers of monocytes in peripheral blood before the isolation and in the sample of monocytes isolated from the peripheral blood were counted according to the following conditions.

Each sample ($3 \times 10^5$ cells) was analyzed for a cell surface marker by flow cytometry. As the marker, CD14, which is a marker of a monocyte, was used. FIG. 1 shows the results. As shown in FIG. 1, comparison between (A) before isolation of monocytes and (B) after isolation of monocytes reveals that the isolation step considerably increases the number of monocytes relative to the total number of cells in a sample (before isolation: 534 cells, after isolation: 2938 cells) to condense the monocytes in the sample.

Example 2

Proliferation of Monocytes

The cancer patient-derived monocytes ($CD14^+$ monocytes and $CD16^+$ monocytes) isolated by the method described above were cultured in a monocyte proliferating culture medium containing the monocyte proliferating agent (Flt-3L was used in this Example) of the present invention according to the following conditions.

Composition of Monocyte Proliferating Culture Medium

Serum-free synthetic culture medium for lymphocytes (X-VIVO 15, Takara Bio Inc.)

Flt-3L (Cellgenix GmbH): 2000 IU/mL

GM-CSF (Miltenyi Biotec GmbH): 1000 IU/mL

Gentamycin: 50 ng/mL

5% Autologous plasma (plasma collected from each cancer patient)

Isolated monocytes were added to the monocyte proliferating culture medium at $2 \times 10^5$ cells/mL of culture medium and were cultured under conditions of 37° C. and 5% $CO_2$ for 3 days. On the fourth day of the culture, the culture medium was replaced by a monocyte differentiating culture medium (1) described in Example 3, and culture was further continued for 8 days. On the 12th day of the culture, the culture medium was replaced by a monocyte differentiating culture medium (2) described in Example 3, and culture was further continued for 3 days. That is, the total culture period was 14 days.

Monocytes were collected at the start of the culture and on the 3rd, 6th, 11th, and 14th days of the culture and were stained with trypan blue, followed by counting the number of cells under a microscope. The results are shown in FIG. 2. As shown in FIG. 2, the monocytes proliferated to about $2 \times 10^6$ cells/mL on the 3rd day of the culture. At this point of time, it is possible to subject the sample to the differentiation step. Furthermore, it can be expected to obtain $10^7$ cells/mL or more of dendritic cells also in the differentiation step by performing the culture in the presence of the monocyte proliferating agent of the present invention.

Example 3

Differentiation of Monocytes

The monocytes prepared above were cultured according to the following conditions.

Composition of Monocyte Differentiating Culture Medium (1)

A culture medium for differentiating monocytes into immature dendritic cells was prepared by adding 1000 IU IL-4 (Miltenyi Biotec GmbH) to the monocyte proliferating culture medium. Hereinafter, this culture medium is referred to as "monocyte differentiating culture medium (1)".

Composition of Monocyte Differentiating Culture Medium (2)

A culture medium for differentiating immature dendritic cells into mature dendritic cells was prepared by further adding the following components to the monocyte differentiating culture medium (1). Hereinafter, this culture medium is referred to as "monocyte differentiating culture medium (2)".

IL-1β (Miltenyi Biotec GmbH): 10 ng/mL

IL-6 (Miltenyi Biotec GmbH): 1000 IU/mL

PGE2 (Cayman Chemical Company): 1 µg/mL

TNF-α (Miltenyi Biotec GmbH): 20 ng/mL 0.1 KE picibanil chloride (Chugai Pharmaceutical Co., Ltd.)

Gentamycin: 50 ng/mL

5% Autologous plasma (plasma collected from each cancer patient)

Proliferated monocytes (i.e., monocytes prepared by culture under the conditions in Example 2 for 3 days) were differentiated into immature dendritic cells by culturing the monocytes in the monocyte differentiating culture medium (1) under the same conditions as those for proliferation of monocytes for 8 days. At the time of completion of the culture for 8 days, the immature dendritic cells were pulsed with an antigen peptide.

The resulting immature dendritic cells were differentiated into mature dendritic cells by culturing the immature dendritic cells in the monocyte differentiating culture medium (2) under the same conditions as those for proliferation of monocytes for 3 days.

Figure 3A:
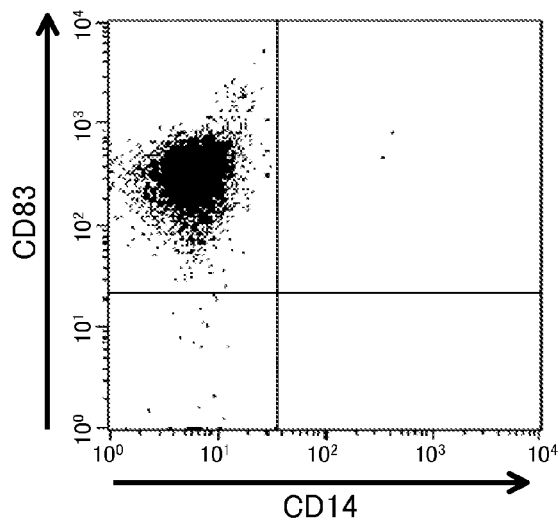
FIG. 3 includes graphs (A) and (B) showing differentiation of monocytes proliferated with the monocyte proliferating agent of the present invention into mature dendritic cells and a graph (C) showing that the mature dendritic cells prepared in (A) and (B) have antigen-presenting ability.
Figure 3C:
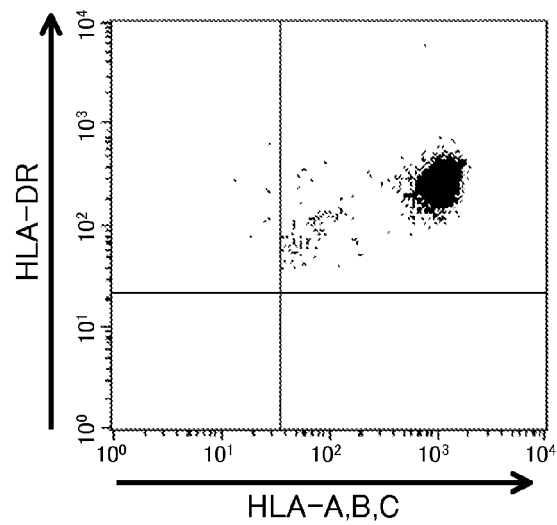
Figure 3B:
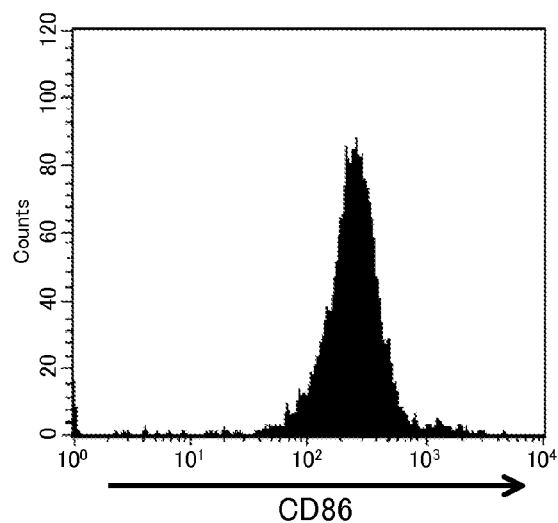

The resulting mature dendritic cells were analyzed for a cell surface marker by flow cytometry. As the marker, CD83, which is a marker of a mature dendritic cell, and CD14, which is a marker of a monocyte, were used. The results are shown in FIG. 3(A). The number of the resulting mature dendritic cells was analyzed using CD83, which is a marker of a mature dendritic cell, as the marker by flow cytometry. The results are shown in FIG. 3(B). As shown in FIGS. 3(A) and 3(B), the cells after differentiation did not include cells expressing CD14 (i.e., monocytes), but included cells expressing CD83 (i.e., mature dendritic cells). These results demonstrate that the monocytes were differentiated into mature dendritic cells.

The antigen-presenting ability of the resulting mature dendritic cells was analyzed using MHC class I molecules (HLA-A, B, and C) and MHC class II molecules (HLA-DR) as the markers by flow cytometry. The results are shown in FIG. 3(C). As shown in FIG. 3(C), the resulting mature dendritic cells expressed MHC class I molecules and MHC class II molecules and were therefore demonstrated to have antigen-presenting ability.

Example 4

Investigation of Influence of Each Cytokine on Proliferation of Monocytes

Influence of each monocyte proliferating agent (Flt-3L, IL-3, or IFN-γ) of the present invention and each cytokine (SCF, IFN-α, or IFN-β) on proliferation of monocytes was investigated according to the following conditions.

Monocytes isolated according to the method described in Example 1 were added to a culture medium in a 96-well petri dish in an amount of $1 \times 10^3$ cells/well and were cultured under conditions of 37° C. and 5% $CO_2$ for 6 days. The composition of the culture medium was as follows. Culture medium composition Serum-free synthetic culture medium for lymphocytes (X-VIVO 15, Takara Bio Inc.)

Cytokines were used in combinations according to the matrix shown in Table 1 (wherein the amount of each cytokine used was as follows).

Flt-3L: 2000 IU/mL
IL-3: 1000 IU/mL
IFN-γ: 10 ng/mL
SCF: 10 ng/mL
IFN-α: 10 ng/mL
IFN-β: 10 ng/mL
GM-CSF: 1000 IU/mL
IL-4: 1000 IU/mL

In Table 1, the term "growth factor" is a collective term for the monocyte proliferating agents (Flt-3L, IL-3, and IFN-γ) of the present invention and cytokines (SCF, IFN-α, and IFN-β).

The number of cells after completion of the culture was visually observed under a microscope, and the influence of each cytokine on the proliferation of monocytes was judged by comparison with the results under conditions of "growth factor free" and "GM-CSF/IL-4 free". The results are shown in Table 1. The criteria are as follows:
±: no change,
+: proliferation of monocytes was slightly accelerated,
++: proliferation of monocytes was accelerated, and
+++: proliferation of monocytes was notably accelerated.

TABLE 1

|  | GM-CSF/IL-4 free | GM-CSF addition | GM-CSF/IL-4 addition |
|---|---|---|---|
| Growth factor free | − | ++ | ++ |
| Flt-3L addition | + | +++ | +++ |
| IL-3 addition | + | +++ | +++ |
| IFN-γ addition | + | +++ | +++ |
| SCF addition | ± | ± | ± |
| IFN-α addition | ± | ± | ± |
| IFN-β addition | ± | ± | ± |

As shown in Table 1, the monocyte proliferating agent (Flt-3L, IL-3, or IFN-γ) of the present invention accelerates proliferation of monocytes. Furthermore, a combination of the monocyte proliferating agent of the present invention and GM-CSF significantly accelerates proliferation of monocytes.

Example 5

Investigation of Vital Cell Ratio of Monocytes

The vital cell ratio of dendritic cells prepared by differentiation of monocytes proliferated with the monocyte proliferating agent of the present invention was investigated according to the following conditions.

About 25 mL of peripheral blood was collected from the arm of each of 20 cancer patients. Monocytes were isolated from the collected peripheral blood as in Example 1. Subsequently, the monocytes were allowed to proliferate as in Example 2, and the resulting monocytes were differentiated into mature dendritic cells as in Example 3.

The resulting mature dendritic cells were stained with trypan blue, followed by measurement of the total number of cells (total number of the resulting mature dendritic cells) and the vital cell ratio. The results are shown in Table 2. The vital cell ratio was calculated by the following expression:

Vital cell ratio (%)=the total number of vital cells(the number of unstained cells)/the total number of cells(the sum of the number of stained cells and the number of unstained cells)×100

TABLE 2

|  | Total number of cells($\times 10^7$) | Vital cell ratio |
|---|---|---|
| Patient 1 | 1.05 | 97.2% |
| Patient 2 | 1.09 | 96.5% |
| Patient 3 | 1.10 | 97.0% |
| Patient 4 | 1.15 | 97.0% |

TABLE 2-continued

| | Total number of cells(×10⁷) | Vital cell ratio |
|---|---|---|
| Patient 5 | 1.03 | 97.0% |
| Patient 6 | 1.01 | 97.3% |
| Patient 7 | 1.03 | 98.1% |
| Patient 8 | 1.04 | 97.3% |
| Patient 9 | 1.23 | 97.5% |
| Patient 10 | 1.04 | 97.7% |
| Patient 11 | 1.06 | 97.9% |
| Patient 12 | 1.17 | 96.7% |
| Patient 13 | 1.10 | 98.7% |
| Patient 14 | 1.14 | 97.8% |
| Patient 15 | 1.07 | 97.1% |
| Patient 16 | 1.12 | 97.1% |
| Patient 17 | 1.03 | 97.9% |
| Patient 18 | 1.05 | 98.2% |
| Patient 19 | 1.11 | 96.7% |
| Patient 20 | 1.02 | 97.8% |

As shown in Table 2, the present invention can be expected to stably provide a high cell count such as $1.0 \times 10^7$ or more and a vital cell ratio of about 97% or more.

The invention claimed is:

1. A method of in vitro proliferation of monocytes comprising
   isolating monocytes from a peripheral blood sample;
   culturing the isolated monocytes in a proliferating culture medium thereby proliferating the isolated monocytes, wherein the proliferating culture medium comprises about 500 to about 2000 IU/ml of GM-CSF, and
   at least one cytokine selected from the group consisting of (a) IFN-γ in an amount of about 50 to 2500 IU/ml, (b) IL-3 in an amount of about 500 to about 3000 IU/ml, and (c) Flt-3L in an amount of about 1000 to 3000 IU/ml.

2. The method of claim 1, wherein the isolated monocytes comprise a mixture containing monocytes and a leukocyte component other than monocytes.

3. The method of claim 1, wherein the method further comprises a reduction step of reducing the content of a component other than monocytes in the peripheral blood sample to isolate the monocytes.

4. The method of claim 3, wherein the reduction is performed using a magnetic bead having a higher affinity to at least one of monocytes, leukocyte components other than monocytes, plasma, and erythrocytes.

5. The method of claim 3, wherein the isolated monocytes are obtained from 100 mL or less of peripheral blood.

6. The method of claim 3, wherein the method does not comprise a cryopreservation step of cryopreserving the isolated monocytes.

7. The method according to claim 1, wherein the isolated monocytes comprises CD14+ monocytes and/or CD16+ monocytes.

8. A method of producing dendritic cells comprising:
   isolating monocytes from a peripheral blood sample;
   culturing the isolated monocytes in a proliferating culture medium thereby proliferating the isolated monocytes, wherein the proliferating culture medium comprises about 500 to about 2000 IU/ml of GM-CSF, and
   at least one cytokine selected from the group consisting of (a) IFN-γ in an amount of about 50 to 2500 IU/ml, (b) IL-3 in an amount of about 500 to about 3000 IU/ml, and (c) Flt-3L in an amount of about 1000 to 3000 IU/ml; and
   differentiating the proliferated monocytes into dendritic cells by subjecting the proliferated monocytes to a differentiating culture medium, wherein the differentiating culture medium comprises GM-CSF and IL-4.

9. The method of claim 8, wherein in the differentiating step, the differentiating culture medium further comprises at least one of Flt-3L, IL-3, and IFN-γ.

10. The method of claim 8, the method further comprising a pulse step of pulsing the dendritic cells.

11. A method of producing a dendritic cell vaccine comprising:
    producing dendritic cells according to the method of claim 8; and
    preparing a dendritic cell vaccine from the dendritic cells.

12. The method of claim 11, wherein the method does not comprise a cryopreservation step of cryopreserving at least one of the monocytes and the dendritic cells.

13. The method of claim 11, wherein the monocytes are isolated from body fluid collected from a subject to whom the dendritic cell vaccine is administered.

* * * * *